(12) United States Patent
Nakazawa et al.

(10) Patent No.: US 7,533,954 B2
(45) Date of Patent: May 19, 2009

(54) PRINTING MEDIA TYPE DISCRIMINATION APPARATUS AND METHOD, AND PRINTING APPARATUS

(75) Inventors: Koichiro Nakazawa, Kanagawa (JP); Akihiro Mouri, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 940 days.

(21) Appl. No.: 10/340,683

(22) Filed: Jan. 13, 2003

(65) Prior Publication Data

US 2003/0137679 A1 Jul. 24, 2003

(30) Foreign Application Priority Data

Jan. 22, 2002 (JP) ............................. 2002-013395

(51) Int. Cl.
*B41J 29/38* (2006.01)

(52) U.S. Cl. ........................... 347/16; 347/19; 347/105

(58) Field of Classification Search ................. 347/105, 347/19, 16, 5, 9; 356/429
See application file for complete search history.

(56) References Cited

U.S. PATENT DOCUMENTS

| | | | |
|---|---|---|---|
| 5,139,339 A | | 8/1992 | Courtney et al. |
| 5,852,499 A | | 12/1998 | Tomita et al. |
| 2003/0001939 A1 | * | 1/2003 | Scofield et al. ............. 347/105 |

FOREIGN PATENT DOCUMENTS

| | | |
|---|---|---|
| DE | 197 57 416 | 7/1999 |
| EP | 0 612 977 | 8/1994 |
| EP | 0 703 443 | 3/1996 |
| EP | 0 911 699 | 4/1999 |
| EP | 1 034 937 | 9/2000 |
| JP | 2-56375 | 2/1990 |
| JP | 5-330696 | 12/1993 |
| JP | 6-15861 | 1/1994 |
| JP | 6-56313 | 3/1994 |
| JP | 6-201412 | 7/1994 |
| JP | 7-69481 | 3/1995 |
| JP | 8-48438 | 2/1996 |
| JP | 8-171312 | 7/1996 |
| JP | 8-259038 | 10/1996 |
| JP | 10-198174 | 7/1998 |
| JP | 11-990 | 1/1999 |
| JP | 2000-302291 | 10/2000 |
| JP | 2001-180843 | 7/2001 |

* cited by examiner

*Primary Examiner*—Lam S Nguyen
(74) *Attorney, Agent, or Firm*—Fitzpatrick, Cella, Harper & Scinto

(57) ABSTRACT

The invention can discriminate, with accuracy and reliability, a variety of printing media such as plain paper, coated paper, glossy paper and OHP sheet. Preferably, light emitting devices and light receiving devices are employed to detect the fiber orientation and gloss-level in the printing media surface. Based on this detection result, the type of each printing medium is decided.

19 Claims, 10 Drawing Sheets

| TYPE OF THE PRINTING MEDIUM | FIRST DETECTING MEANS (DETECTING FIBER ORIENTATION) | SECOND DETECTING MEANS (DETECTING GLOSS-LEVEL) | CATEGORY |
|---|---|---|---|
| | LIGHT RECEIVING DEVICE (16, 18, 20) | LIGHT RECEIVING DEVICE (18) | |
| PLAIN PAPER | THE RECEIVED LIGHT IS RELATIVELY STRONG, AND ITS INTENSITY VARIES BETWEEN THE LIGHT RECEIVING DEVICES. | THE RECEIVED LIGHT IS WEAK. | A |
| COATED PAPER | THE RECEIVED LIGHT IS RELATIVELY STRONG, AND ITS INTENSITY VARIES LITTLE BETWEEN THE LIGHT RECEIVING DEVICES. | THE RECEIVED LIGHT IS WEAK. | B |
| GLOSSY PAPER | THE RECEIVED LIGHT IS RELATIVELY WEAK, AND ITS INTENSITY VARIES LITTLE BETWEEN THE LIGHT RECEIVING DEVICES. | THE RECEIVED LIGHT IS RELATIVELY STRONG. | C |
| OHP SHEET | THE RECEIVED LIGHT IS VERY WEAK, AND ITS INTENSITY DOES NOT VARY BETWEEN THE LIGHT RECEIVING DEVICES. | THE RECEIVED LIGHT IS STRONG. | D |

FIG.3

| TYPE OF THE PRINTING MEDIUM | | FIRST DETECTING MEANS (DETECTING FIBER ORIENTATION) | | | SECOND DETECTING MEANS (DETECTING GLOSS-LEVEL) |
|---|---|---|---|---|---|
| CATEGORY | MERCHANDIZE NUMBER | LIGHT RECEIVING DEVICE (16) | LIGHT RECEIVING DEVICE (18) | LIGHT RECEIVING DEVICE (20) | LIGHT RECEIVING DEVICE (18) |
| PLAIN PAPER | PB (CANON MAKE) | 3.1 | 3.8 | 3.6 | 1.3 |
| COATED PAPER | HR101 (CANON MAKE) | 3.7 | 3.9 | 3.6 | 1.4 |
| GLOSSY PAPER | GP301 (CANON MAKE) | 3.0 | 2.9 | 2.7 | 3.9 |
| OHP SHEET | CF102 (CANON MAKE) | 1.0 | 0.8 | 0.7 | 7.2 |

FIG.4

PRINTING MEDIA TYPE DISCRIMINATION APPARATUS AND METHOD, AND PRINTING APPARATUS

This application claims priority from Japanese Patent Application No. 2002-013395 filed Jan. 22, 2002, which is incorporated hereinto by reference.

BACKGROUND OF THE INVENTION

1. Filed of the Invention

The invention relates to a printing media type discrimination apparatus and method, and a printing apparatus.

2. Description of the Related Art

In printing apparatuses (image formation apparatuses) of electronic photographing, thermal printing, wire-dot and ink-jet types that print images on the printing surface of a printing medium by adhering colored toner and ink thereto, the resulting image quantity significantly depends on the type of the printing medium. Thus, before starting image printing, a printing mode suitable for the type of the selected printing medium is set, and images are then printed in accordance with the selected printing mode.

In order to set a printing mode suitable for the selected printing medium, a variety of methods have been proposed that automatically discriminate the type of each printing medium installed in the printing apparatus.

For example, there is a method that automatically identifies the type of the printing medium, based on its transparency. In such a technique, an optic sensor sensitive to reflection and another optic sensor sensitive to transparency are individually installed in the printing media transport path. Then the opaque printing media such as plain paper are identified with the detection output from the reflection-sensitive sensor, while the transparent OHP (overhead projector) sheet (hereinafter "OHP sheet") is identified with the detection output from the transparency-sensitive sensor.

Meanwhile, a printing-media front/rear side discriminating method is disclosed in Japanese Patent Application Laid-open No. 6-015861 (1994), for example. Provided that such a printing medium is used that has different gloss levels between its front and rear sides, the side is recognized from the difference in the gloss level.

A method to distinguish the OHP sheet from plain paper is disclosed in Japanese Patent Application Laid-open Nos. 2-056375 (1990) and 6-056313 (1994), for example. Such a method utilizes the difference in random reflection between the OHP sheet and plain paper. Namely, when the medium is irradiated with a detection light beam, the degree of random reflection on the surface is smaller in the OHP sheet than in plain paper. In this technique, a light source (light emitting device) that emits a detection light beam and a plurality of light receiving devices that receive the reflected light are installed on one side of the printing surface of the printing medium. These light receiving devices are configured to receive the regular reflection and random reflection. In such a configuration, when the intensity of regular reflection from the printing surface is large, it indicates that the printing medium is an OHP sheet. On the other hand, when the intensity of random reflection from the printing surface is large, it indicates that the printing medium is plain paper.

Furthermore, Japanese Patent Application Laid-open No. 6-056313 (1994) shows a method using a transparency-sensitive sensor and a reflection-sensitive sensor to discriminate the printing media types. In this method, a pair of light receiving devices are installed to sandwich the printing medium, and a light source emitting the detection light beam is installed on one side of the printing medium. When the printing medium comes in the light path between the light source and one of the light receiving devices installed across the printing medium, if the light receiving device does not send a detection output, the medium is decided to be plain paper. Meanwhile, if the other light receiving device sends a detection output, the medium is decided to be an OHP sheet.

Moreover, in Japanese Patent Application Laid-open No. 10-198174 (1998), a light source emitting a detection light beam and a light receiving device receiving the detection light beam reflected by the surface of the printing medium are installed, correlated with each other, so that the light path of the detection light beam makes a predetermined incident angle and a reflection angle against the surface of the printing medium. In this technique, whether the printing medium is plain paper or an OHP sheet is determined from the intensity of the regular reflection of the detection light beam that the light receiving device has received.

As an automatic printing media type discriminating method other than the above, Japanese Patent Application Laid-open No. 7-069481 (1995), for example, discloses a method utilizing a change in capacitance of the printing medium. Japanese Patent Application Laid-open No. 8-259038 (1996) discloses a method utilizing the rigidity of the printing medium.

In addition, as another automatic printing media type discriminating method, Japanese Patent Application Laid-open Nos. 6-201412 (1994) and 11-000990 (1999) disclose a method by which an identifier unique to each printing medium is installed in each printing medium and read by an optic method.

Most of the above automatic printing media type discriminating methods are, however, related to techniques for distinguishing the opaque plain paper from the transparent OHP sheet. Thus those methods have difficulty automatically discriminating a variety of media types, for example, distinguishing plain paper from coated paper with reliability.

For example, the method disclosed in Japanese Patent Application Laid-open No. 6-015861 (1994) is only applicable to printing media of which front and rear sides have different gloss levels, because it relies on the difference in the gloss level in the front and rear sides of the printing medium.

Likewise, the technique disclosed in Japanese Patent Application Laid-open Nos. 2-056375 (1990) and 6-056313 (1994) has difficulty distinguishing plain paper from coated paper because both media provide weak regular reflection of the detection light beam. As a measure to solve this problem, a plurality of thresholds may be set for signals obtained by the light receiving devices to compare and discriminate the media types. Nevertheless, because there are many types of plain paper and coated paper sharing the same threshold, it is very difficult to set a single threshold for each paper type, and thus the accuracy of media type discrimination becomes very low.

As a result, when the printing media types are identified by a conventional method relying on the transparency of the medium, only two media types—the OHP sheet or otherwise—are identified. Meanwhile, when the printing media types are identified by a conventional method relying on the gloss level, only two media types—whether glossy paper, glossy film and OHP sheet, or plain paper and coated sheet—are identified.

Even if a conventional method relying on transparency and that relying on the gloss level are combined, identified are just up to three types, namely whether the OHP sheet, or glossy media (glossy paper and glossy film) or non-glossy media (plain paper and coated paper).

On the other hand, according to the method disclosed in Japanese Patent Application Laid-open No. 10-198174 (1998), it only identifies, when the printing media are stored in a paper holder, whether the printing medium at the top is plain paper or an OHP sheet. Thus, it cannot discriminate other media types.

SUMMARY OF THE INVENTION

The present invention has been made to solve the above problems, and of its objects is to provide a printing media type discriminating apparatus, method and a printing apparatus that can automatically discriminate a variety of printing media types such as plain paper, coated paper, glossy paper and OHP sheet, with high accuracy and reliability.

In the first aspect of the present invention, there is provided a printing media type discriminating apparatus comprising:

a first detecting means for detecting the fiber orientation in the surface of the printing medium;

a second detecting means for detecting the gloss level in the surface of the printing medium; and a discriminating means for discriminating printing media types based on the fiber orientation and gloss level in the printing media surface detected by the first and second detecting means.

In the second aspect of the present invention, there is provided a printing apparatus that performs printing on a printing medium according to a specified printing media type, comprising:

a first detecting means for detecting the fiber orientation in the surface of the printing medium;

a second detecting means for detecting the gloss level in the surface of the printing medium;

a discriminating means for discriminating printing media types based on the fiber orientation and gloss level in the printing media surface detected by the first and second detecting means; and a means for comparing the printing media type decided by the discriminating means with the specified printing media type and for preventing printing if the decided media type does not agree with the specified type.

In the third aspect of the present invention, there is provided a printing apparatus that performs printing on a printing medium in a printing mode according to a printing media type, comprising:

a first detecting means for detecting the fiber orientation in the surface of the printing medium;

a second detecting means for detecting the gloss level in the surface of the printing medium;

a discriminating means for discriminating printing media types based on the fiber orientation and gloss level in the printing media surface detected by the first and second detecting means; and a means for setting the printing mode corresponding to the printing media type identified by the discriminating means.

In the fourth aspect of the present invention, there is provided a printing media type discriminating method comprising the steps of:

a first step of detecting the fiber orientation in the surface of the printing medium;

a second step of detecting the gloss level in the surface of the printing medium; and a step of discriminating printing media types based on the fiber orientation and gloss level in the printing media surface detected at the first and second steps.

In the fifth aspect of the present invention, there is provided a printing media type discriminating apparatus comprising:

a calculating means for detecting the intensity of diffused reflection light reflected by the surface of the printing media by using a plurality of light receiving devices, and for calculating a parameter obtained from the intensity of diffused reflection light detected by each of the plurality of light receiving devices;

a detecting means for detecting the gloss level in the surface of the printing medium; and a discriminating means for discriminating the printing media types based on the parameter calculated by the calculating means and on the gloss level detected by the detecting means.

According to the present invention, the fiber orientation and gloss level in the surface of each printing medium are detected, and the media type is determined from this detection result. Then it is possible to automatically discriminate, with accuracy and reliability, a variety of media types such as plain paper, coated paper, glossy paper and OHP sheet.

To be more specific, because the fiber orientation and the gloss level in the surface of each printing medium are detected, at least four media types providing different pairs of fiber orientation and gloss level, namely, plain paper, glossy media (including glossy paper and glossy film), coated paper (media having an ink acceptance layer on a base material and a low gloss level) and transparent media (including OHP sheets), can be detected with accuracy and reliability.

The above and other objects, effects, features and advantages of the present invention will become more apparent from the following description of embodiments thereof taken in conjunction with the accompanying drawings.

BRIEF DESCRIPTION OF THE DRAWINGS

FIG. 3 is a table illustrating the relations between the printing media types and criteria for discrimination in the discriminating apparatus installed in the printing apparatus of FIG. 1;

FIG. 4 is a table illustrating the relations between the printing media types and detection outputs from the light receiving device in the discriminating apparatus installed in the printing apparatus of FIG. 1;

DETAILED DESCRIPTION OF PREFERRED EMBODIMENTS

Now the embodiments of the present invention will be described with reference to the accompanying drawings.

First Embodiment

Figure 1:
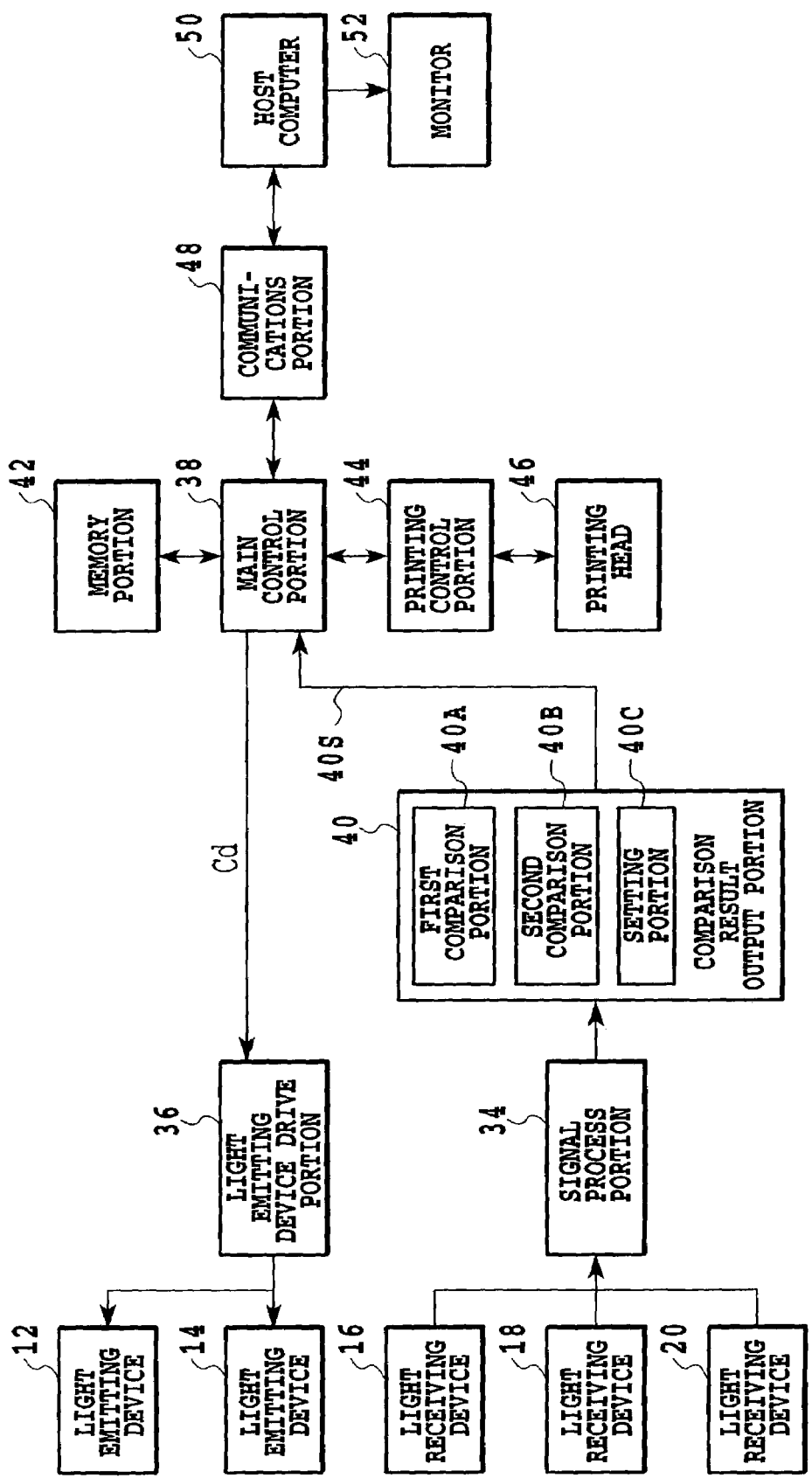
FIG. 1 is a block diagram illustrating the control system for the printing apparatus according to a first embodiment of the present invention.

FIG. 1 is a block diagram of the control system for the inkjet printing apparatus working as the printing apparatus of a first embodiment of the present invention. The inkjet printing apparatus has a discriminating apparatus that determines the type of each printing medium.

In the inkjet printing apparatus of FIG. 1, reference numeral 46 denotes a printing head portion that ejects specific ink for printing onto the printing surface (hereinafter, occasionally called "surface") of a printing medium that will be described later. Reference numeral 44 denotes a printing control portion that controls the printing operation of the printing head portion 46, based on the supplied image data and printing control data. Reference numeral 38 denotes a main control portion that controls the transport system that intermittently transports the printing medium to the position opposing to the ink ejection portion of the printing head portion 46, the printing system including the printing control portion 44, and a discriminating apparatus that will be described later.

A memory portion 42 that stores data and sends data selectively based on control signals is connected to the main control portion 38. The memory portion 42 holds an operation program data used for operation control by the main control portion 38, image data for the image to be formed on the printing surface of the printing medium, data correlating the types of printing media held in the printing apparatus and discrimination results that will be described later, and other data.

The relations between the type of the printing medium selectively held in the printing apparatus and the discrimination results that will be described later become those shown in FIG. 3. Namely, the comparison results provided by the comparison output portion that will be described later are related with the media types of plain paper, coated paper, glossy paper and OHP sheet. In this example, these four types of media are classified into A, B, C and D.

For such discrimination of printing media, the outputs from first and second detecting means that will be described later are used. The first detecting means detects the fiber orientation in the surface of the printing medium and provides the detection result, while the second detecting means detects the gloss (gloss level) of the surface of the printing medium and provides the detection result.

The feature of the first detecting means is to measure the variation in the intensities of light beams reflected at the same angle. In general, the surface of plain paper is characterized by fiber orientation, machine direction or paper moire. The spot on plain paper irradiated by the detection light beam emitted from a light source returns a strong light reflection in the direction of the fiber orientation, while causes weak reflection in a direction perpendicular to the direction of the fiber orientation. On the other hand, in coated paper and glossy paper, which have an ink acceptance layer coated on the base material such as plain paper, the variation of the intensities of light beams reflected at the same angle is small than that seen in plain paper. The OHP sheet is entirely irrelevant to the fiber orientation because it uses a resin film represented by polyethylene terephthalate or the like. Thus it is possible to decide whether the printing medium is plain paper or not by detecting the fiber orientation of the printing medium.

The main control portion 38 is connected to a host computer 50 via a communications portion 48 installed in the bi-directional transmission line. The host computer 50 produces image data corresponding to the image to be formed on the printing surface of the printing medium, and sends each specific image data piece to the main control portion 38 via the communications portion 48 at a predetermined timing. Also the host computer 50 sends control data sets needed to control the inkjet printing apparatus to the main control portion 38 via the communications portion 48.

A monitor 52 for displaying the operation status of the inkjet printing apparatus is connected to the host computer 50. The monitor 52 is, for example, a CRT or liquid crystal display.

Figure 2A:
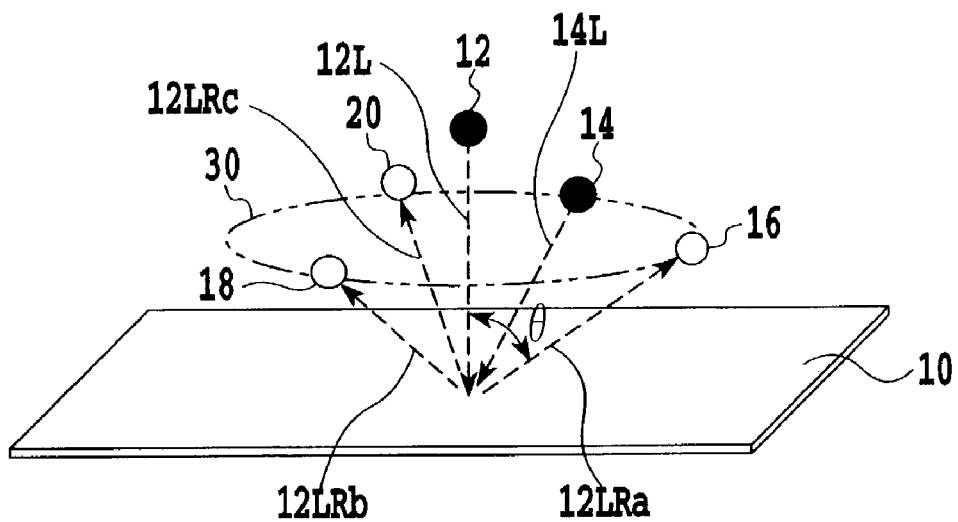
FIG. 2A is a perspective view illustrating the structure of the detecting unit of the discriminating apparatus installed in the printing apparatus of FIG. 1.
Figure 2B:
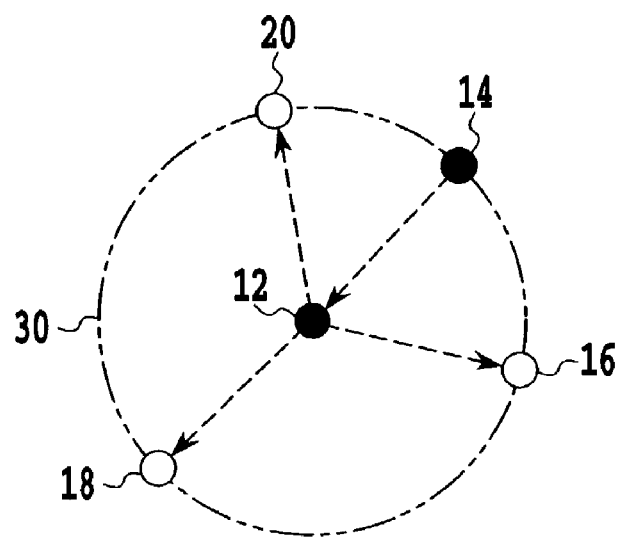
FIG. 2B is its plan view.

The discriminating apparatus installed in the inkjet printing apparatus has a detection portion comprising light emitting devices 12, 14 and light receiving devices 16, 18, 20. As shown in FIGS. 2A and 2B, the light emitting devices 12, 14 are arranged to face the printing surface of a printing medium 10 positioned in the inkjet printing apparatus, and emit detection light beams onto the printing surface of the printing medium 10. The light receiving devices 16, 18, 20 receive the light beams 12LRa, 12LRb, 12LRc emitted from the light emitting device 12 and reflected at the same angle θ by the printing surface. The light emitting device 14 and the light receiving device 18 are positioned so that the regular reflection beam coming from the light emitting device 14 and reflected by the printing surface may be received by the light receiving device 18. Reference numeral 30 in FIG. 2B denotes a virtual reference circle of which center is the light emitting device 12. In the present embodiment, the light receiving devices 16, 18, 20 and the light emitting device 14 are positioned on the reference circle 30. The light receiving devices 16, 18, 20 are arrayed at equal intervals on the reference circle 30. In FIG. 2B, the light emitting device 12 is positioned on a normal line passing the center of the reference circle 30 and standing in a direction of a normal line perpendicular to the surface of the printing medium.

The light emitting devices 12, 14 are, for example, high-brightness red LED (BR5364X: Stanley make) having a peak wavelength of 660 nm. The light receiving devices 16, 18, 20 are, for example, silicon phototransistors (KS853: Sinko-Denshi make). The light emitting devices 12, 14 may be those of which wavelengths lie in the visible light range or out of the visible range. Semiconductor lasers and LED can be used as such light emitting devices.

On the other hand, the light receiving devices 16, 18, 20 are those sensitive to the wavelength range of the light emitting devices 12, 14. They may be semiconductor devices such as silicon photodiodes and silicon phototransistors. The light receiving devices 16, 18, 20 each may have an output portion (not shown) made of an amplifying circuit such as the Darlington circuit.

The light emitting devices 12, 14 are connected to a light emitting device drive portion 36. The light emitting device drive portion 36 drives the individual light emitting devices 12, 14 based on a control signal Cd sent from the main control portion 38. The light emitting devices 12, 14 become ready to work when a current of about 10 mA is supplied.

The signal processing portion 34 connected to each of the output portions of the light receiving devices 16, 18, 20 conducts a predetermined digital processing on the detection signals from the light receiving devices 16, 18, 20 and provides detection data. The signal processing portion 34 provides the detection data that has been subject to a digital conversion to the comparison result output portion 40.

The first comparison portion 40A in the comparison result output portion 40 receives the detection data from the individual light receiving devices 16, 18, 20 in accordance with the predetermined timing for lighting the light emitting device 12. Then the comparison portion 40A calculates the variation in the detection data (variation in the received light intensity) provided by the individual light receiving devices 16, 18, 20, compares the calculation with a predetermined threshold (hereinafter, occasionally called "first threshold"), and sends out the comparison result (first comparison output).

The second comparator 40B in the comparison out portion 40 compares the detection data of the light receiving device 18, in accordance with the predetermined timing of lighting the light emitting device 14, with a predetermined thresholds (hereinafter, occasionally called "second threshold", "third threshold"), and sends out the comparison result (second comparison output).

The comparison result output portion 40 has a setting portion 40C that sets the first, second and third thresholds for the comparison portions 40A, 40B. The setting portion 40C sets, for example, ±0.5(V) as the first threshold for the first comparison portion 40A with respect to the variation in the detection data of the individual light receiving devices 16, 18, 20. Also the setting portion 40C sets two levels, 3 and 5(V), as the second and third thresholds for the second comparison portion 40B with respect to the detection data of the light receiving devices 18.

The data selection-transmit portion 40S connected to the comparison portions 40A, 40B selectively sends the comparison outputs from the comparison portions 40A, 40B to the main control portion 38, correlating the outputs to the individual printing media.

FIG. 4 shows an example of such media type discrimination for the printing medium 10 in the above configuration. In FIG. 4, four media, namely, plain paper, coated paper, glossy paper and OHP sheet, are used as materials for the printing medium 10. Specifically, PB (Canon make), HR101 (Canon make), GP301 (Canon make) and CF102 (Canon make) have been employed. FIG. 4 demonstrates the detection data provided by the first detecting means for detecting the fiber orientation in the media surface and the detection data provided by the second detecting means for detecting the gloss level in the medium surface of the printing medium 10.

When the first detecting means works, the light emitting device 12 emits a light beam, and the light receiving devices 16, 18, 20 provide the detection signal (output voltage (V)). The detection signal is digitally converted by the signal processing portion 34, and sent to the comparison result output portion 40 as detection data (voltage (V)). The comparison portion 40A of the comparison result output portion 40 calculates the maximum value in the variations in the detection data (corresponding to differences in output voltage between the detection signals), and compares the calculated variation with the first threshold (±0.5(V)). If the calculated variation is equal to or larger than the first threshold, it is decided that there is an intensity difference in the light beams reflected at the same reflection angle, and the first comparison output is sent out. In the example of FIG. 4, if the printing medium 10 is plain paper, the calculated variation becomes −0.7(V) (=3.1−3.8(V)) that is equal to or larger than the first threshold (±0.5(V)). Then it is decided that there is an intensity difference in the light beams reflected at the same reflection angle, and the first comparison output is sent out.

On the other hand, if the calculated variation is smaller than the first threshold, it is decided that there is no difference in the intensities of light beams reflected at the same reflection angle, and the second comparison output is sent out. In the example of FIG. 4, if the printing medium 10 is not plain paper, the calculated variation becomes 0.3(V) that is smaller than the first threshold (±0.5(V)). Namely, if it is coated paper, the calculated variation is 0.3(V) (=3.9−3.6(V)); if it is glossy paper, it is 0.3(V) (=3.0−2.7(V)); and if OHP sheet, then 0.3(V) (=1.0−0.7(V)). In these cases, it is decided that there is no difference in the intensities of light beams reflected at the same angle, and the second comparison output is sent out.

In this manner, by comparing the variation in the detection data provided by the light receiving devices 16, 18, 20 in the first detecting means with the first threshold, it can be decided whether the printing medium 10 is plain paper or not. If the printing medium 10 is decided to be plain paper, the first comparison output is sent out, while the second comparison output is sent output if the medium is decided to be other than plain paper.

When the second detecting means works, the light emitting device 14 emits a light beam, and the light receiving device 18 provides a detection signal (output voltage (V)). The detection signal is digitally converted by the signal processing portion 34, and sent to the comparison result output portion 40 as detection data (voltage (V)) for checking the gloss level. The second comparison portion 40B compares this detection data (gloss-level detection data) with the second threshold (3(V)) and third threshold (5(V)). If the detection data is equal to or larger than the third threshold (5(V)), it is decided that the printing medium has a very high gloss level, and a third comparison output is sent out. Meanwhile, if the detection data is equal to or larger than the second threshold (3(V)), and at the same time, smaller than the third threshold (5(V)), it is decided that the printing medium 10 is glossy, and a fourth comparison output is sent out. If the detection data is smaller than the second threshold (3(V)), it is decided that the printing medium 10 is not glossy, and a fifth comparison output is sent out.

As indicated in FIG. 4, if the printing medium 10 is OHP sheet, the gloss-level detection data becomes 7.2(V) that is larger than the third threshold (5(V)). Then it is decided that the printing medium has a very high gloss level, and the third comparison output is sent out. Meanwhile, if the printing medium 10 is glossy paper, the gloss-level detection data becomes 3.9(V), being larger than the second threshold (3(V)), but smaller than the third threshold (5(V)). Then it is decided that the printing medium is glossy, and the fourth comparison output is sent out. If the printing medium 10 is coated paper, the gloss-level detection data becomes 1.4(V), being smaller than the second threshold (3(V)). Then it is decided that the medium is not glossy, and the fifth comparison output is sent out.

In this manner, by comparing the gloss-level detection data provided by the light receiving devices 18 in the second detecting means with the second and third thresholds, it can be decided whether the printing medium 10 is plain paper, OHP sheet, glossy paper or coated paper. If the printing medium 10 is decided to be an OHP sheet, the third comparison output is sent out, and if decided to be glossy paper, then the fourth comparison output is sent out, while the fifth comparison output is sent output if the medium is decided to be coated paper.

The data selection-transmit portion 40S sends the comparison output from the comparison result output portion 40 to the main control portion 38 based on the data request signal from the main control portion 38.

The main control portion 38 refers to data shown in FIG. 3, and identifies the four types of the printing media based on the comparison output from the data selection-transmit portion 40S. To be more specific, when it has received the third comparison output indicating a very high gloss level and the second comparison output indicating no difference in the intensity of light reflected at the same reflection angle, it decides that the printing medium 10 is OHP sheet (category D). If it has received the fourth comparison output indicating a high gloss level and the second comparison output indicating no difference in the intensity of light reflected at the same reflection angle, it decides that the printing medium 10 is glossy paper (category C).

After distinguishing between the OHP sheet and glossy paper, the main control portion 38 identifies the other feature of the printing medium 10. Namely, if it has received the fifth comparison output indicating a low gloss level and the second comparison output indicating no difference in the intensity of light reflected at the same reflection angle, it decides that the printing medium 10 is coated paper (category B). Meanwhile, if it has received the fifth comparison output indicating a low gloss level and the first comparison output indicating a difference in the intensity of light reflected at the same reflection angle, it decides that the printing medium 10 is plain paper (category A).

In this way, it is possible to determine whether the printing medium is OHP sheet, glossy paper or otherwise, at least based on the third, fourth and fifth comparison outputs from the comparison portion 40B. In the next step, based on the first and second comparison outputs from the comparison portion 40A, the rest two media types, namely, coated paper and plain paper can be distinguished. As a result, plain paper (PB: Canon make), coated paper (HR101: Canon make), glossy paper (GP301: Canon make) and OHP sheet (CF102: Canon make) can be distinguished from each other. In short, four media types, plain paper, coated paper, glossy paper and OHP sheet can be identified.

The comparison portion 40 and the main control portion 38 may be comprised of, for example, a micro computer. With reference to the flowchart shown in FIG. 5, an example of the programs such a micro computer executes will be described below.

Figure 5:
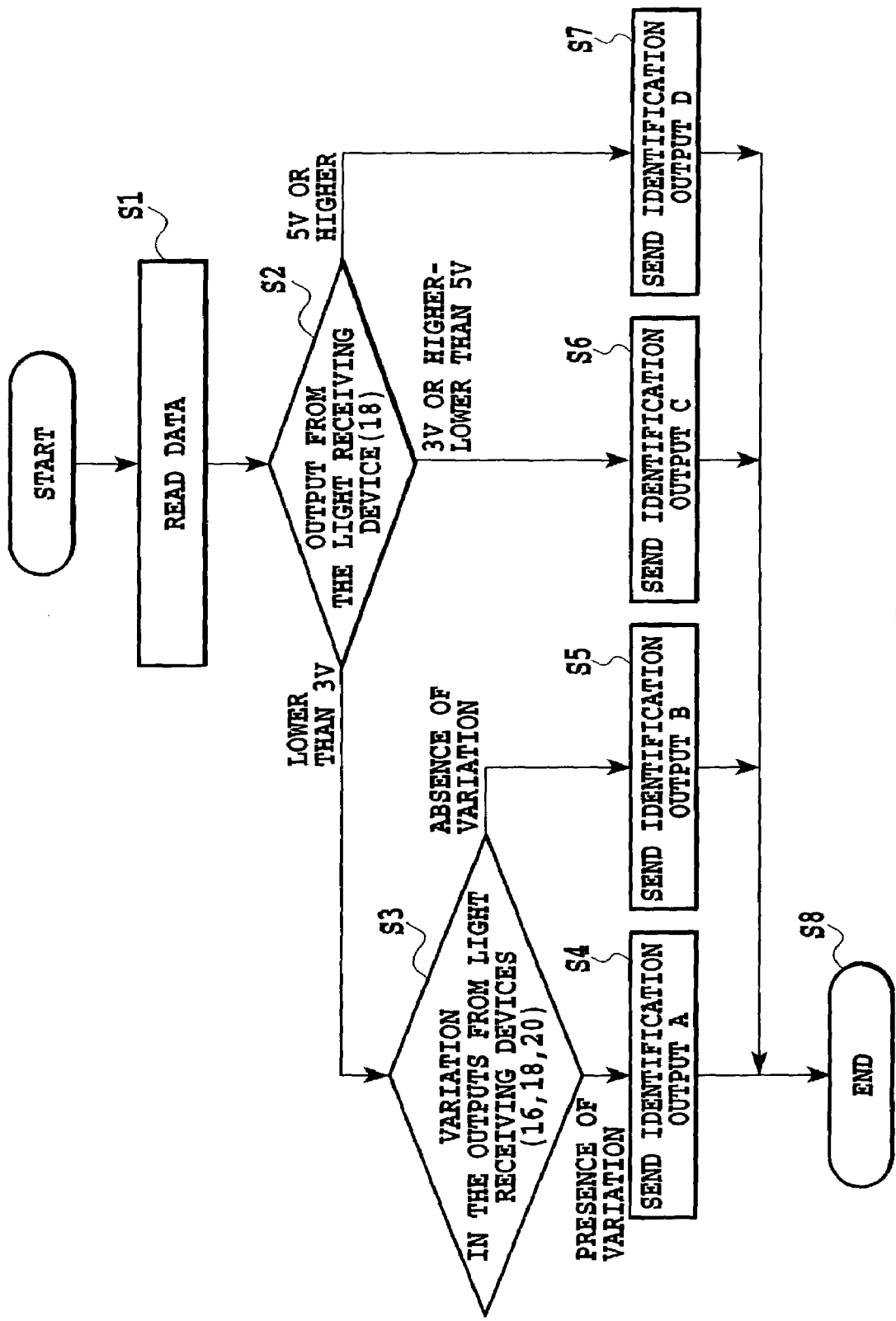
FIG. 5 is a flowchart illustrating the operations of the discriminating apparatus installed in the printing apparatus of FIG. 1.

In FIG. 5, at step S1 after the start, the detection data provided by the individual light receiving devices 16, 18, 20 is acquired as the information about the printing surface of the printing medium 10 that will be identified. At the next step S2, the gloss-level detection data provided by the light receiving device 18 is compared with the second and third thresholds (3(V), 5(V)). If the gloss-level detection data is smaller than the second threshold (3(V)), it proceeds to step S3, and compares the variation in the detection data of the light receiving devices 16, 18, 20 (the data representing the intensity of light reflected at the same reflection angle) with the first threshold (±0.5(V)). If the variation in the detection data is ±0.5(V) or higher, it proceeds to step S4, and ends the program after deciding that the printing medium 10 is plain paper and sending out a discrimination output A. Meanwhile, if the variation in the detection data is smaller than the first threshold at step S3, it proceeds to step S5, and ends the program after deciding that the printing medium 10 is coated paper and sending out a discrimination output B.

Further, at step S2, if the gloss-level detection data is equal to or larger than the second threshold (3(V)), and, at the same time, smaller than the third threshold (5(V)), it proceeds to step S6, and ends the program after deciding that the printing medium 10 is coated paper and sending out a discrimination output C. Meanwhile, at step S2, if the gloss-level detection data is equal to or larger than the third threshold (5(V)), it proceeds to step S7, and ends the program after deciding that the printing medium 10 is OHP sheet and sending out a discrimination output D.

Second Embodiment

Figure 6:
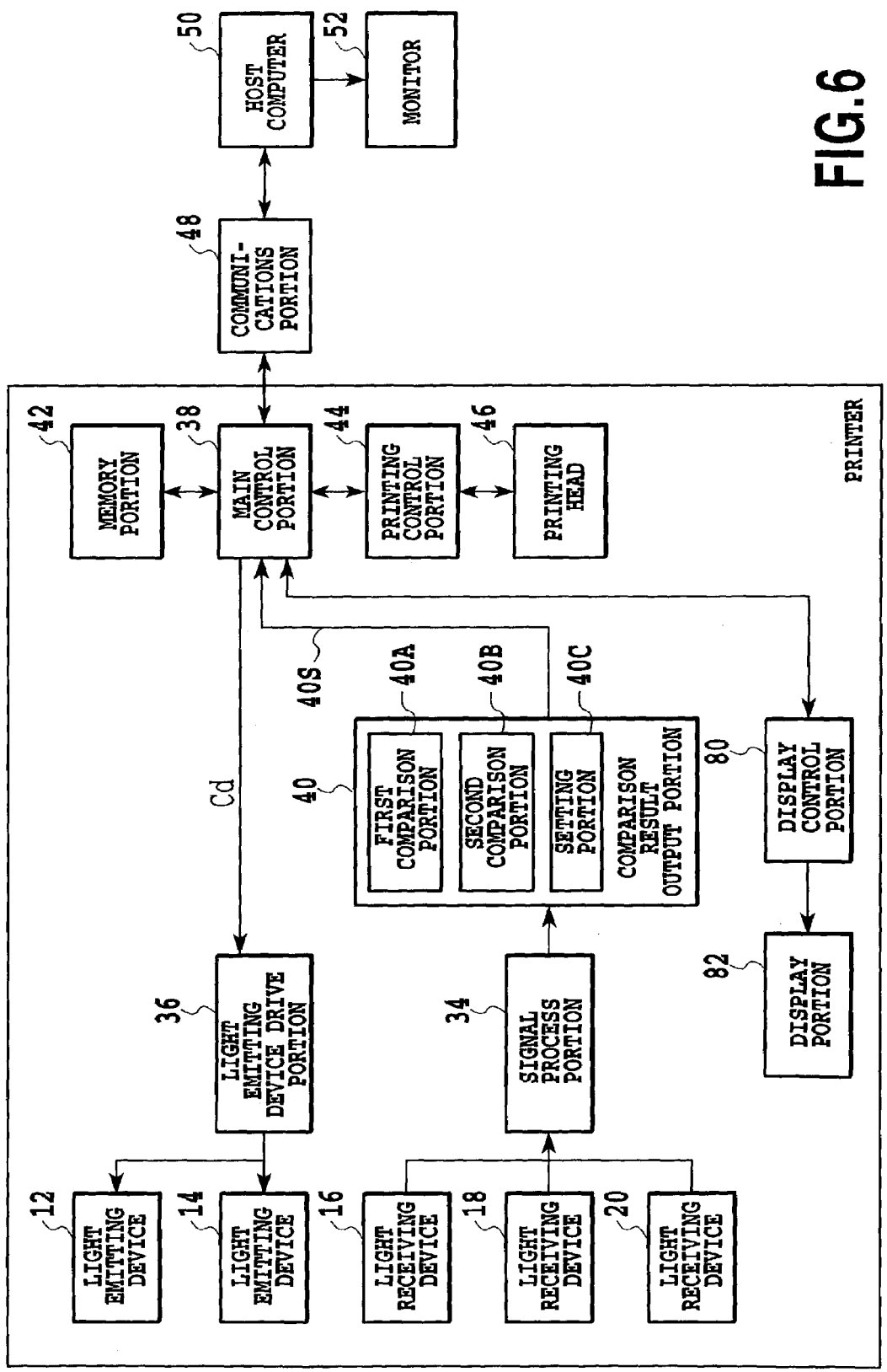
FIG. 6 is a block diagram illustrating the control system for the printing apparatus according to a second embodiment of the present invention.

FIG. 6 is a block diagram illustrating the control system for the inkjet printing apparatus equipped with a discriminating apparatus according to a second embodiment of the present invention. Similar elements have similar numerals in FIG. 6 and FIG. 1, and their descriptions are not repeated here.

There are relations between the printing media types selectively installed in the printing apparatus and the above discrimination outputs, as shown in FIG. 3, much similar to the foregoing embodiment. Thus, in this embodiment as well, the printing medium is decided to be one of the four media types (A, B, C and D).

A display portion 82 is connected to the main control portion 38 via a display control portion 80. The display portion 82 displays a warning to the effect that the type of the printing medium installed in the printing apparatus does not agree with the media type data provided to the host computer 50.

The host computer 50 is equipped with a printing mode selection portion (not shown) for selecting the printing mode based on the discrimination outputs A-D provided by the main control portion 38. The data regarding the printing mode selected by the printing mode selection portion is sent to the main control 38 via the communications portion 48. The printing mode selection portion selects, from a plurality of printing modes, a printing mode matching the printing medium type, as the printing mode suitable for the printing head portion 46, based on the data representing the medium type sent from the main control portion 38. Individual printing modes are determined with reference to, for example, the moving speed of the printing head portion 46 suitable for printing the image onto each printing medium and the amount of ink injection.

A monitor 52 connected to the host computer 50 displays the operation status of the inkjet printing apparatus based on the display data sent from the host computer 50. The monitor 52 is, for example, a CRT or a liquid crystal display.

Further, when the host computer 50 has selectively set a media type of the printing medium, the main control portion 38 compares the selected media type with the discrimination result on the media type determined by the comparison output from the comparison result output portion 40. If there is a disagreement in the comparison, the main control portion 38 sends to the printing control portion 44 a control signal to cancel printing, and a control signal to the display controller 80 to display on the display portion 82 a warning urging to cancel printing. Then, in any case where the decision of the type of the printing medium based on the comparison output from the comparison result output portion 40 disagrees with the printing media type selectively set by the host computer 50, the display unit 82 issues a warning.

In this way, because the comparison result output portion 40 identifies without fail the media type of the printing medium actually installed in the printing apparatus, the display unit 82 displays a warning if this printing media type does not agree with that set by the user, in other words, the media type set by the host computer 50. In this way, if there is a disagreement in the printing media type information, a warning is displayed so that the printing may not be carried out by a printing mode unsuitable for the current printing medium. As a result, when an inkjet printing apparatus is shared by a plurality of host computers connected to each other via data bus lines, for example, it is possible to build a warning display system that notices the user of a problem by issuing a warning that urges the user to cancel printing before starting printing.

As an experiment, the inventor issued orders to print a sample image on each of the plain paper, coated paper, glossy paper and an OHP sheet, with the right and wrong printing modes. As a result, when the wrong printing mode was specified, a warning indicating the wrong printing was issued before starting printing. On the other hand, when the right printing mode was specified, the sample image was successfully printed on the individual printing media.

Meanwhile, when the host computer 50 does not specify a media type, the image mode selection portion of the host computer 50 selects a printing mode suitable for the current printing medium, as described before, based the decision of the printing media type relying on the comparison output from the comparison result output portion 40. Therefore, it is possible, for example, to build a system that automatically selects the suitable printing mode for the inkjet printing apparatus that is controlled by a standalone host computer. In an experimental verification, the inventor made sure that, when an order to print a sample image, the image was successfully printed on each of the plain paper, coated paper, glossy paper and an OHP sheet.

Third Embodiment

Figure 7A:
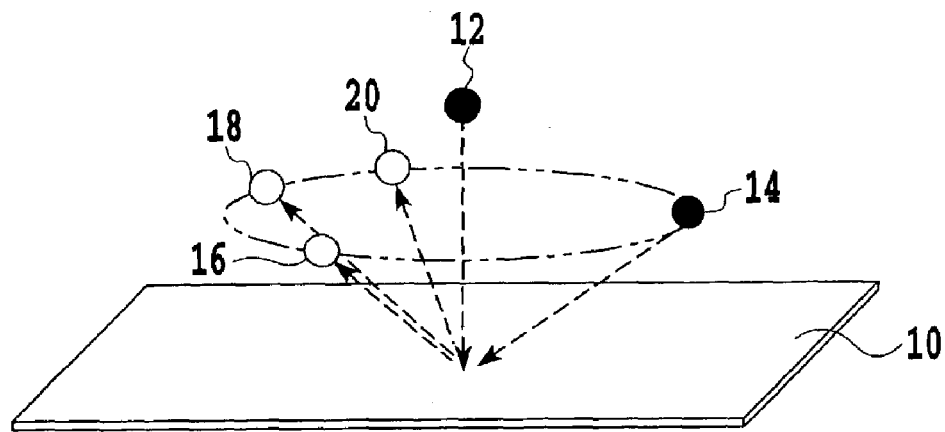
FIG. 7A is a perspective view illustrating the schematic structure of the detecting unit of the discriminating apparatus of a third embodiment of the present invention.
Figure 7B:
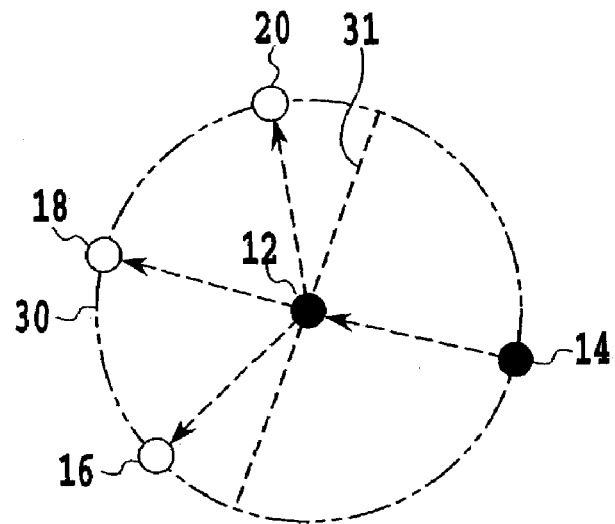
FIG. 7B is its plan view.

FIGS. 7A and 7B show another embodiment of the detection portion used in the printing media type discriminating apparatus. The other constitutes other than the detection portion are the same as those in the foregoing embodiments.

In the detection portion of the embodiment, the light receiving devices 16, 18 and 20 are positioned in only half the whole directions, instead of being positioned in the whole directions of the same reflection angle as in the above embodiments. Reference numeral 31 denotes a virtual reference line, and this reference line 31 divides the circular reference line 30 into two arcs in FIG. 7B. In this embodiment, the light receiving devices 16, 18 and 20 are arranged in one of the arcs 30. For saving the light receiving devices in detecting the fiber orientation, it is not necessary to measure the reflection light in the whole directions of the same reflection angle like the above embodiments. Instead, the fiber orientation can be detected by measuring the reflection light in half the whole directions like the present embodiment.

Fourth Embodiment

Figure 8A:
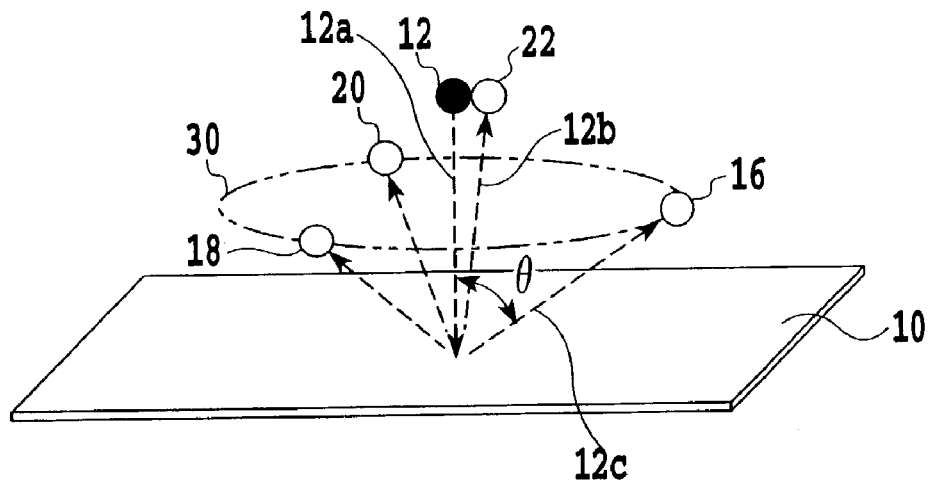
FIG. 8A is a perspective view illustrating the schematic structure of the detecting unit of the discriminating apparatus of a fourth embodiment of the present invention.
Figure 8B:
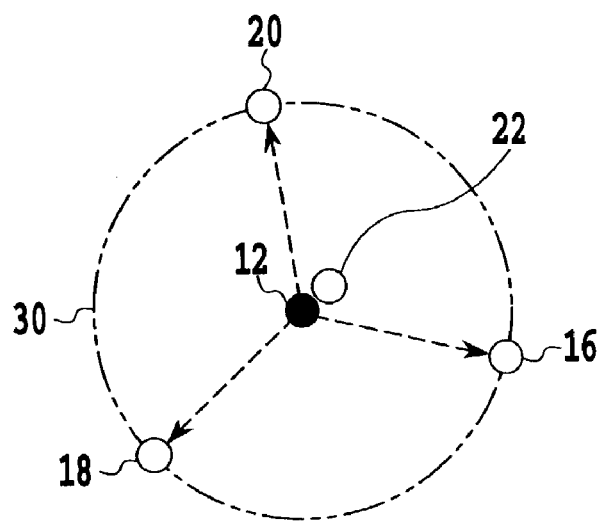
FIG. 8B is its plan view.

FIGS. 8A and 8B show another embodiment of the detection portion used in the printing media type discriminating apparatus.

In the detection unit of the embodiment, a light receiving device 22 is additionally installed on behalf of the light emitting device 14. This light receiving device 22, working on behalf of the light receiving device 18, provides a detection signal for producing gloss-level detection data by detecting the reflection light that was emitted from the light emitting device 12 and then reflected by the printing medium.

Fifth Embodiment

Figure 9A:
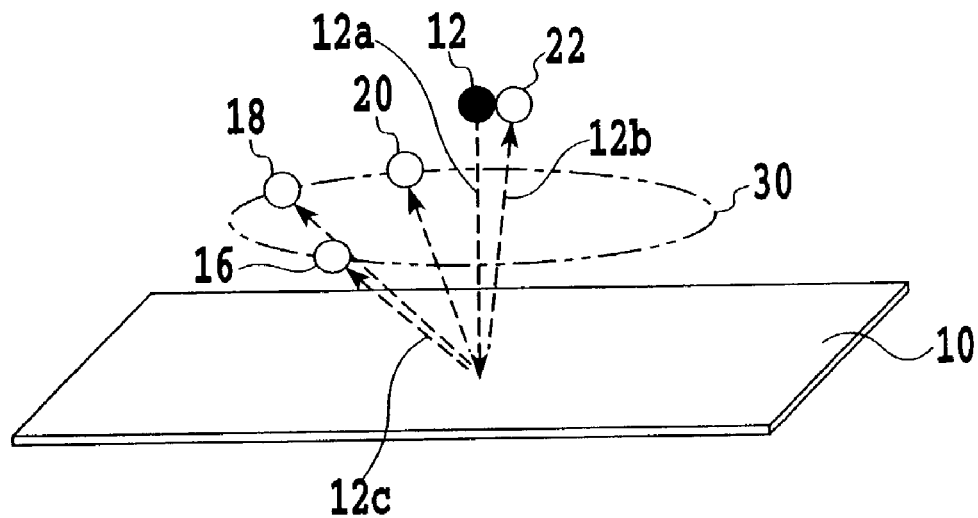
FIG. 9A is a perspective view illustrating the schematic structure of the detecting unit of the discriminating apparatus of a fifth embodiment of the present invention.
Figure 9B:
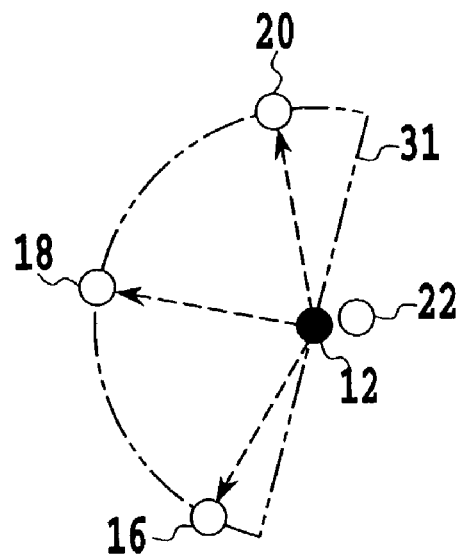
FIG. 9B is its plan view.

FIGS. 9A and 9B show another embodiment of the detection portion used in the printing media type discriminating apparatus.

The detection portion of the present embodiment is a combination of the third and fourth embodiments. Specifically, the light emitting device 14 in the third embodiment is replaced by a light receiving device 22 as employed in the fourth embodiment.

(Another Embodiment of the Detection Portion)

In the detection portions in the foregoing embodiments, the first detecting means for detecting the fiber orientation in the printing media surface and the second detecting means for detecting the gloss-level in the printing medium have shared light emitting and receiving devices. However, each of the first and second detecting means may be functionally separated from each other, equipped with its own light emitting and receiving devices.

Preferably, the light receiving devices of the first detecting means receive reflection light clearly representing the fiber orientation. For this purpose, the reflection angle should be large. Specifically, the reflection angle should be 45 degrees or more but less than 90 degrees, in the normal line direction perpendicular to the surface of the printing medium.

When there is no printing medium installed in the media type detecting position in the detection portion, it is preferable to install a base material in the detecting position. The surface of this base material should be such that well absorbs light of wavelengths of the corresponding light emitting devices, being exposed in the detecting position. When no printing medium is installed, this configuration leads to smaller outputs from the first and second detecting means than those provided when any of the plain paper, coated paper, glossy paper or OHP sheet is installed. With this configuration, the presence/absence of a printing medium can be detected as well. Such a base material absorbing much light should have a high absorbance that is 1 or higher, clearly different from that of general printing media, in the wavelength range of the corresponding light emitting devices. Then, a new category E for such a base material is added to the printing media types A-D.

In the above embodiment of the detection portion, the first detecting means has three light receiving devices to measure the intensity of light reflected at the same reflection angle. Since if the first detecting means has four or more light receiving devices, its function of detecting the intensity of reflection of the same angle does not change. Thus its description is not repeated here.

(Example of a Printing Apparatus)

Figure 10:
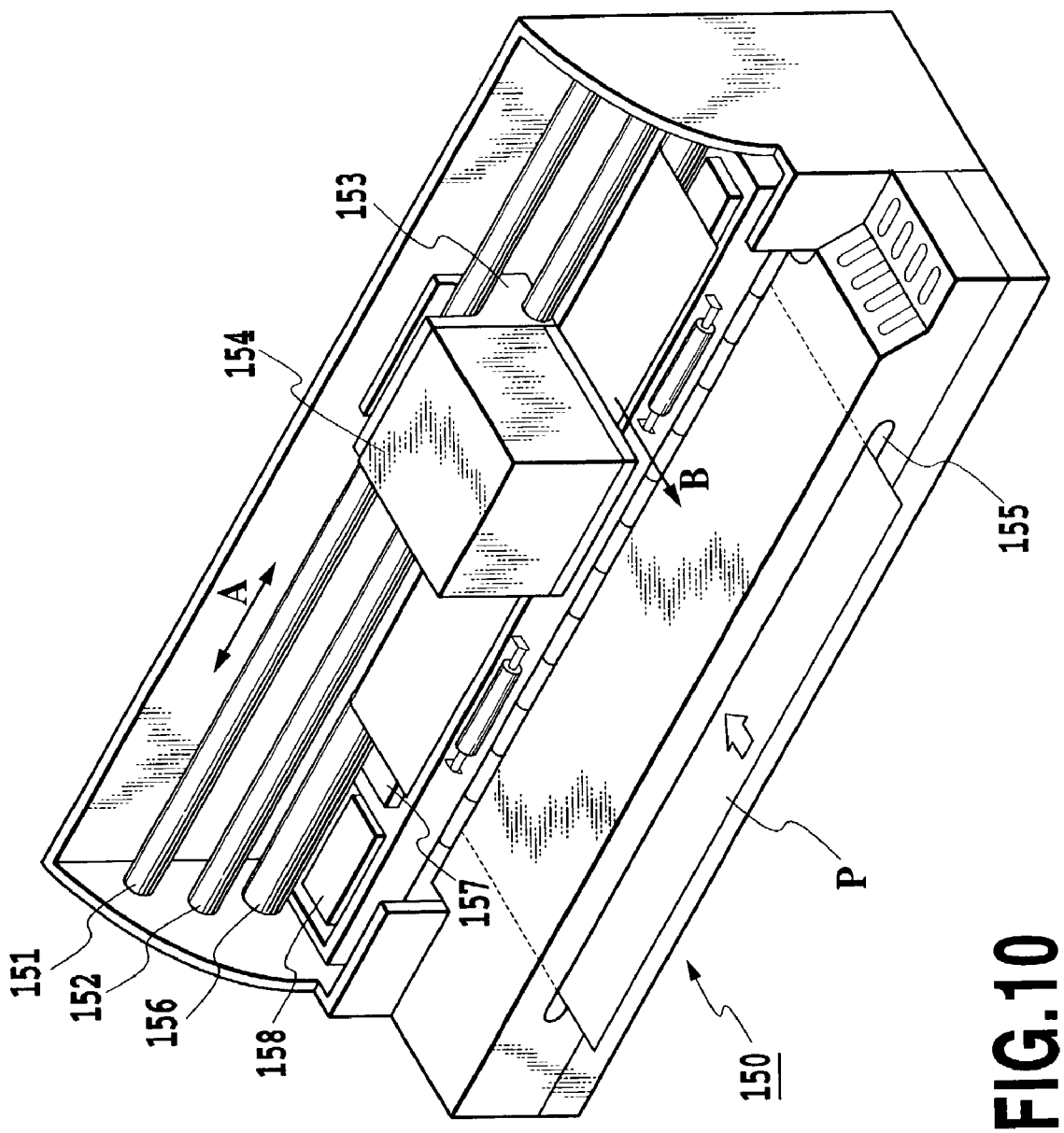
FIG. 10 is a schematic perspective view of a printing apparatus to which the present invention is applicable.

FIG. 10 is a perspective view illustrating the schematic structure of a printing apparatus to which the present invention is applicable.

The printing apparatus 150 of the embodiment is a serial scan type inkjet printing apparatus. Guide shafts 151, 152 movably guide a carriage 153 in the main scanning direction shown by arrow A. The carriage 153 shuttles in the main scanning direction, driven by, for example, a driving force transmission mechanism such as a belt that transmits the force produced in the carriage motor. The carriage 153 has an inkjet printing head (not shown) comprising the printing head portion 46 and an ink tank 154 that supplies ink to the printing head. The printing head and the ink tank 154 may comprise the inkjet cartridge. The inkjet printing head can eject ink from the ink ejection opening, and use thermal energy produced by a thermoelectric converter to eject ink. Specifically, the thermal energy produced by the thermoelectric converter causes the film boiling of ink, and the produced bubbles push ink out of the ink ejection opening. As the method of ejecting ink, a variety of techniques using the Piezo device, for example, can be used.

Paper P as a printing medium is inserted from an inlet 155 on the front side of the printing apparatus, and transported to the sub-scanning direction shown with arrow B by a roller 156 after its transport direction has been reversed. The printing apparatus 150 prints images one after another on paper P by alternately performing a printing operation of ejection ink from the ink ejection opening of the printing head toward the printing area of paper P on a platen 157 while moving the carriage 153 with the mounted printing head, and transporting operation of transporting paper P in the sub-scanning direction as much as a length corresponding to the printing width by the printing operation.

In the left end of the motion range of the carriage 153 in FIG. 10, a recovery unit (recovery processing means) 158 is installed in the position facing the ink ejection opening of the printing head mounted on the carriage 153. The recovery unit 158 has a cap capable of capping the ink ejection opening of the printing head and a pump capable of causing a negative pressure in the cap. The recovery unit 158 conducts a recovery processing (sucking recovery processing) to suck ink out of the ink ejection opening and to maintain the ink ejection from the printing head in a good condition, introducing a negative present in the cap covering the ink ejection opening. It is also possible to conduct the recovery processing (ejecting recovery processing) to maintain ink-ejection performance of the printing head by ejecting ink that is not involved in image printing, from the ink ejection opening to the cap.

The present invention can be applied to a wide range of printing apparatuses using various printing heads other than the inkjet printing head. The invention can also be applied to not only the serial scan type printing apparatus but also the full-line type printing apparatus, for example, equipped with printing heads along the entire width of the printing area of the printing medium.

The present invention has been described in detail with respect to preferred embodiments, and it will now be apparent from the foregoing to those skilled in the art that changes and modifications may be made without departing from the invention in its broader aspects, and it is the intention, therefore, in the appended claims to cover all such changes and modifications as fall within the true spirit of the invention.

What is claimed is:

1. A printing media type discriminating apparatus comprising:
   first detecting means for detecting a fiber orientation in a surface of a printing medium by using a plurality of light receiving devices, the plurality of light receiving devices being positioned so as to receive a plurality of reflection light beams that have been reflected by the printing medium surface at the same reflection angle different from an incident angle, the plurality of reflection light beams being reflected in different directions;
   second detecting means for detecting a gloss level in the surface of the printing medium by using at least one of the plurality of light receiving devices; and
   discriminating means for discriminating printing media types based on the fiber orientation and gloss level in the printing medium surface detected by the first and second detecting means,
   wherein when the gloss level, detected by the second detecting means, is equal to or greater than a predetermined level, the discriminating means discriminates the printing media types based on the gloss level, and when the gloss level is less than the predetermined level, the discriminating means discriminates whether the printing medium is plain paper based on the fiber orientation detected by the first detecting means.

2. A printing media type discriminating apparatus as claimed in claim 1, wherein the second detecting means detects the gloss level in the printing medium surface based on an intensity of a regular reflection light from the printing medium surface.

3. A printing media type discriminating apparatus as claimed in claim 1, wherein the first detecting means has three or more of the light receiving devices.

4. A printing media type discriminating apparatus as claimed in claim 1, wherein
   the first detecting means has a first light source emitting light onto the surface of the printing medium from the position on a normal line perpendicular to the surface of the printing medium in order to cause reflection light that will be received by the plurality of light receiving devices, and
   the second detecting means has a second light source emitting light onto the surface of the printing medium to cause the reflection light that will be received by at least one of the plurality of light receiving devices.

5. A printing media type discriminating apparatus as claimed in claim 1, wherein the plurality of light receiving devices receive the reflection light beams of the same reflection angle from the surface of the printing medium evenly in all directions.

6. A printing media type discriminating apparatus as claimed in claim 1, wherein the plurality of light receiving devices receive the reflection light beams of the same reflection angle from the surface of the printing medium, the plurality of light receiving devices being positioned to one side of a plane bisecting the printing medium and a source of the reflection light beams.

7. A printing media type discriminating apparatus as claimed in claim 1, wherein the plurality of light receiving devices receive the reflection light beams making an angle of 45 degrees or more but less than 90 degrees relative to a normal line perpendicular to the surface of the printing medium.

8. A printing media type discriminating apparatus as claimed in claim 1, wherein the discriminating means identifies the printing medium as one of plain paper, coated paper, glossy paper and OHP sheet, based on the fiber orientation and gloss level in the printing medium surface detected by the first and second detecting means.

9. A printing media type discriminating apparatus as claimed in claim 1, further comprising:
   calculating means for detecting an intensity of diffused reflection light reflected by the surface of a printing medium by using the plurality of light receiving devices, and for calculating a parameter obtained from the intensity of diffused reflection light detected by each of the plurality of light receiving devices,
   wherein the discriminating means discriminates the printing media types based on the parameter calculated by the calculating means and on the gloss level detected by the second detecting means.

10. A printing media type discriminating apparatus as claimed in claim 9, wherein the parameter is the variation in the intensity of diffused reflection light detected by each of the plurality of light receiving devices.

11. A printing media type discriminating apparatus as claimed in claim 9, wherein the calculating means calculates the parameter based on a difference among the intensities of diffused reflection lights detected by the plurality of light receiving devices.

12. A printing media type discriminating apparatus as claimed in claim 1, wherein the plurality of light receiving devices are positioned on a flat surface parallel to the print medium surface and have the same distance from a position of the printing medium surface to which light is emitted.

13. A printing media type discriminating apparatus as claimed in claim 1, wherein the surface of the printing medium reflects an incident light beam emitted from a normal line perpendicular to the surface of the printing medium.

14. A printing apparatus that performs printing on a printing medium according to a specified printing media type, comprising:
  first detecting means for detecting a fiber orientation in the surface of the printing medium by using a plurality of light receiving devices, the plurality of light receiving devices being positioned so as to receive a plurality of reflection light beams that have been reflected by the printing medium surface at the same reflection angle different from an incident angle, the plurality of reflection light beams being reflected in different directions;
  second detecting means for detecting a gloss level in the surface of the printing medium by using at least one of the plurality of light receiving devices;
  discriminating means for discriminating printing media types based on the fiber orientation and gloss level in the printing medium surface detected by the first and second detecting means; and
  means for comparing the printing media type decided by the discriminating means with the specified printing media type and for preventing printing if the decided media type does not agree with the specified type,
  wherein when the gloss level, detected by the second detecting means, is equal to or greater than a predetermined level, the discriminating means discriminates the printing media types based on the gloss level, and when the gloss level is less than the predetermined level, the discriminating means discriminates whether the printing medium is plain paper based on the fiber orientation detected by the first detecting means.

15. A printing apparatus as claimed in claim 14, wherein printing on the printing medium is performed by using a printing head movable relatively over the printing medium.

16. A printing apparatus that performs printing on a printing medium in a printing mode according to a printing media type, comprising:
  first detecting means for detecting a fiber orientation in the surface of the printing medium by using a plurality of light receiving devices, the plurality of light receiving devices being positioned so as to receive a plurality of reflection light beams that have been reflected by the printing medium surface at the same reflection angle different from an incident angle, the plurality of reflection light beams being reflected in different directions;
  second detecting means for detecting a gloss level in the surface of the printing medium by using at least one of the plurality of light receiving devices;
  discriminating means for discriminating printing media types based on the fiber orientation and gloss level in the printing medium surface detected by the first and second detecting means; and
  means for setting the printing mode corresponding to the printing media type identified by the discriminating means,
  wherein when the gloss level, detected by the second detecting means, is equal to or greater than a predetermined level, the discriminating means discriminates the printing media types based on the gloss level, and when the gloss level is less than the predetermined level, the discriminating means discriminates whether the printing medium is plain paper based on the fiber orientation detected by the first detecting means.

17. The printing apparatus as claimed in claim 16, wherein printing on the printing medium is performed by using a printing head movable relatively over the printing medium.

18. A method for discriminating a printing media type by using a plurality of light receiving devices, the plurality of light receiving devices being positioned so as to receive a plurality of reflection light beams that have been reflected by the printing medium surface at the same reflection angle different from an incident angle, the plurality of reflection light beams being reflected in different directions, the method comprising the steps of:
  a first step of detecting a fiber orientation in the surface of the printing medium by using the plurality of light receiving devices;
  a second step of detecting a gloss level in the surface of the printing medium by using at least one of the plurality of light receiving devices; and
  a step of discriminating printing media types based on the fiber orientation and gloss level in the printing medium surface detected at the first and second detecting steps,
  wherein when the gloss level, detected in the second detecting step, is equal to or greater than a predetermined level, the discriminating step discriminates the printing media types based on the gloss level, and when the gloss level is less than the predetermined level, the discriminating step discriminates whether the printing medium is plain paper based on the fiber orientation detected in the first detecting step.

19. A printing media type discriminating method as claimed in claim 18, wherein the fiber orientation and gloss level in the printing medium surface are optically detected at the first and second detecting steps based on the light reflected by the printing medium surface.

* * * * *